United States Patent [19]

Daube, Jr. et al.

[11] Patent Number: 4,697,462
[45] Date of Patent: Oct. 6, 1987

[54] ACTIVE CLOUDWATER COLLECTOR

[75] Inventors: Bruce C. Daube, Jr.; Richard C. Flagan; Michael R. Hoffmann, all of Pasadena, Calif.

[73] Assignee: California Institute of Technology, Pasadena, Calif.

[21] Appl. No.: 867,820

[22] Filed: May 27, 1986

[51] Int. Cl.$^4$ .......................... G01N 1/24; G01N 1/14; G01N 1/18
[52] U.S. Cl. ............................. 73/863.21; 73/863.02; 73/863.31; 73/864.34; 73/170 R; 55/185; 55/259; 55/528
[58] Field of Search ........... 73/863.21, 863.22, 863.23, 73/863.24, 863.25, 863.02, 863.03, 863.31, 864.34, 864.35, 170 R; 55/185, 257 PV, 259, 528

[56] References Cited

U.S. PATENT DOCUMENTS

| | | | |
|---|---|---|---|
| 2,699,679 | 1/1955 | Munger | 73/863.21 |
| 3,462,995 | 8/1969 | Weiss | 73/863.21 |
| 3,593,583 | 7/1971 | Anderson et al. | 73/863.21 X |
| 3,889,532 | 6/1975 | Pilie et al. | 73/863.22 |
| 4,159,635 | 7/1979 | Sehmel | 73/863.22 |
| 4,570,494 | 2/1986 | Dunn et al. | 73/863.22 |

FOREIGN PATENT DOCUMENTS 500504  5/1976  U.S.S.R. ............................ 73/863.22

OTHER PUBLICATIONS

"A Technique for the Experimental Measurement of Collection Efficiency"; Conference on Cloud Physics Fort Collins, Colo., Aug. 24-27, 1970, paper reprint, pp. 139-142; J. R. Adam et al.

"A Linear Impactor for Fog Droplet Sampling"; Atmospheric Environment, vol. 14, No. 7, pp. 797-801; Sandra Fuzzi et al; 1980.

Primary Examiner—Tom Noland
Attorney, Agent, or Firm—Max Geldin

[57] ABSTRACT

A cloud water collector is disclosed comprised of a sampler duct having a plurality of spaced Teflon strands, in the form of screens, mounted across the conduit at an acute angle facing the open inlet of the conduit. Droplets in a cloud sample are drawn into the conduit by a fan located at the back end of the conduit, impact upon the Teflon strands and are drawn down to the lower ends of the strands, where they drop and the accumulated droplets are diverted to a sample bottle for collection. The cloud water collector can be automated to collect a plurality of successive cloud water samples by an automated sampler containing a reservoir into which cloud water obtained in the cloud water collector is discharged. A motor-driven turntable is provided which holds a plurality of sample bottles. When the reservoir is filled to a predetermined volume, apparatus, such as a liquid level sensor, actuates a valve to open same and discharge the liquid sample from the reservoir into one of the bottles at a filling station on the turntable. The valve then closes and the turntable rotates to index the next bottle beneath the reservoir at the filling station, and the operation is repeated to fill the latter bottle. When all of the bottles on the turntable have been filled, the indexing mechanism is deactivated and liquid accumulating in the reservoir is diverted to an overflow bottle.

25 Claims, 17 Drawing Figures

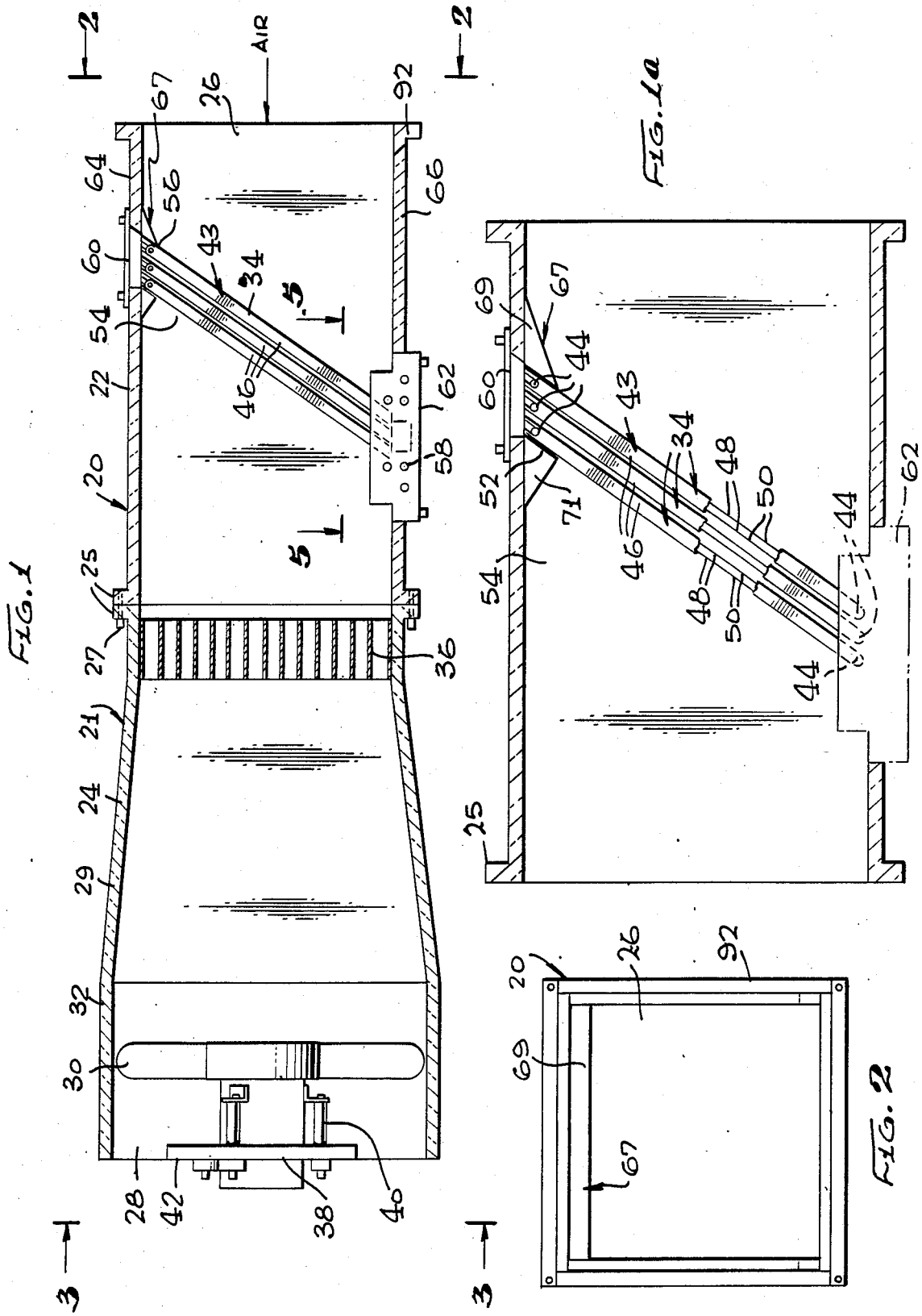

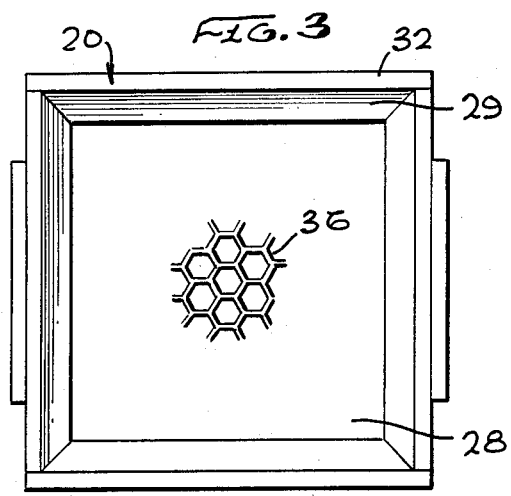
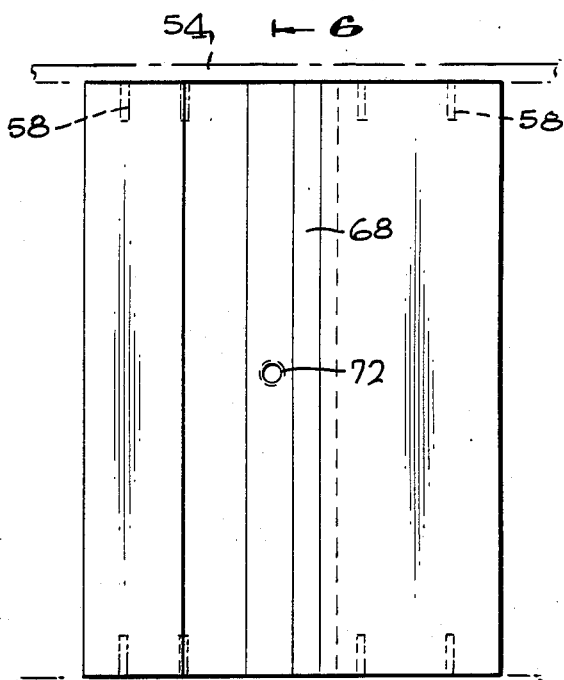
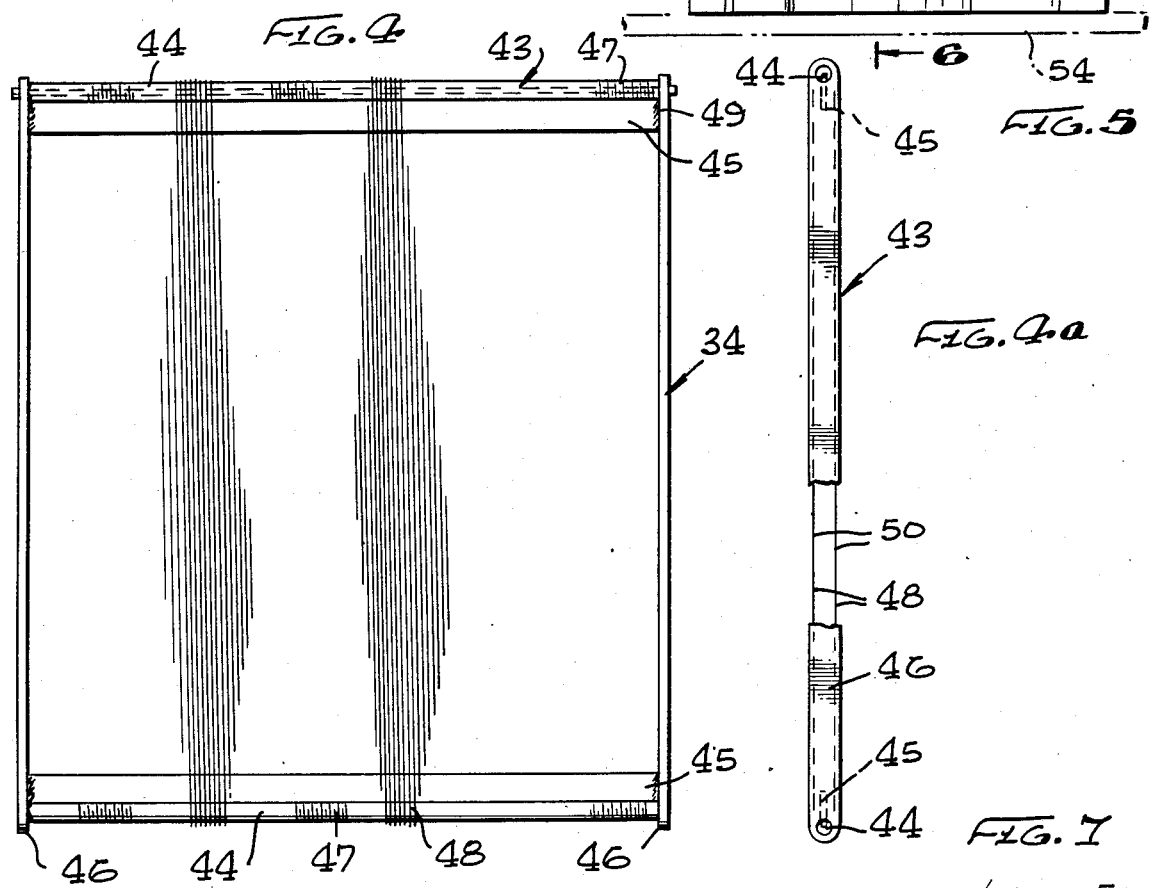
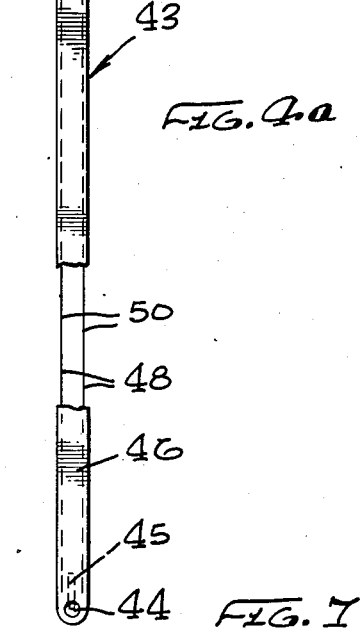
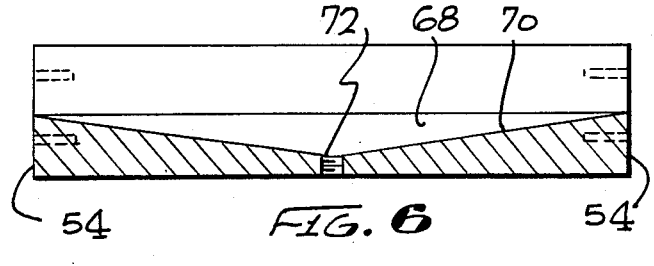
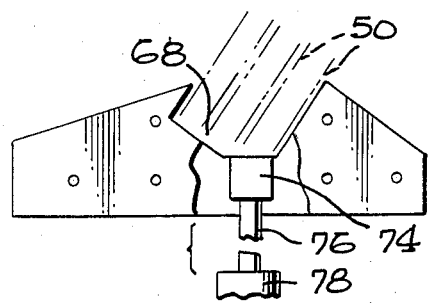

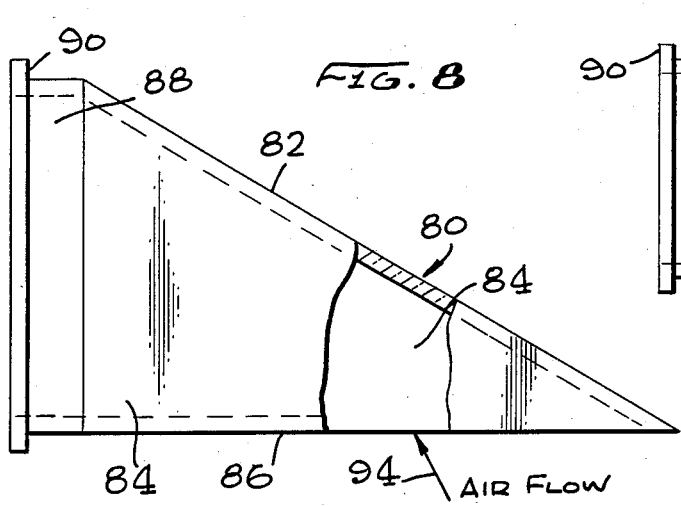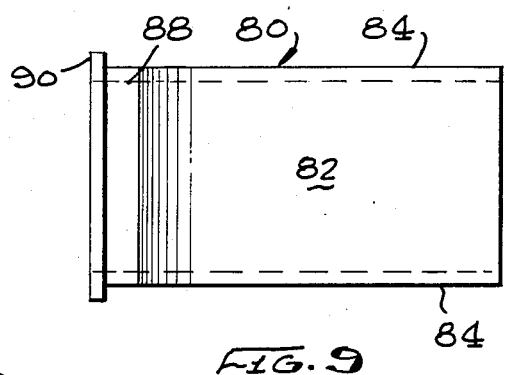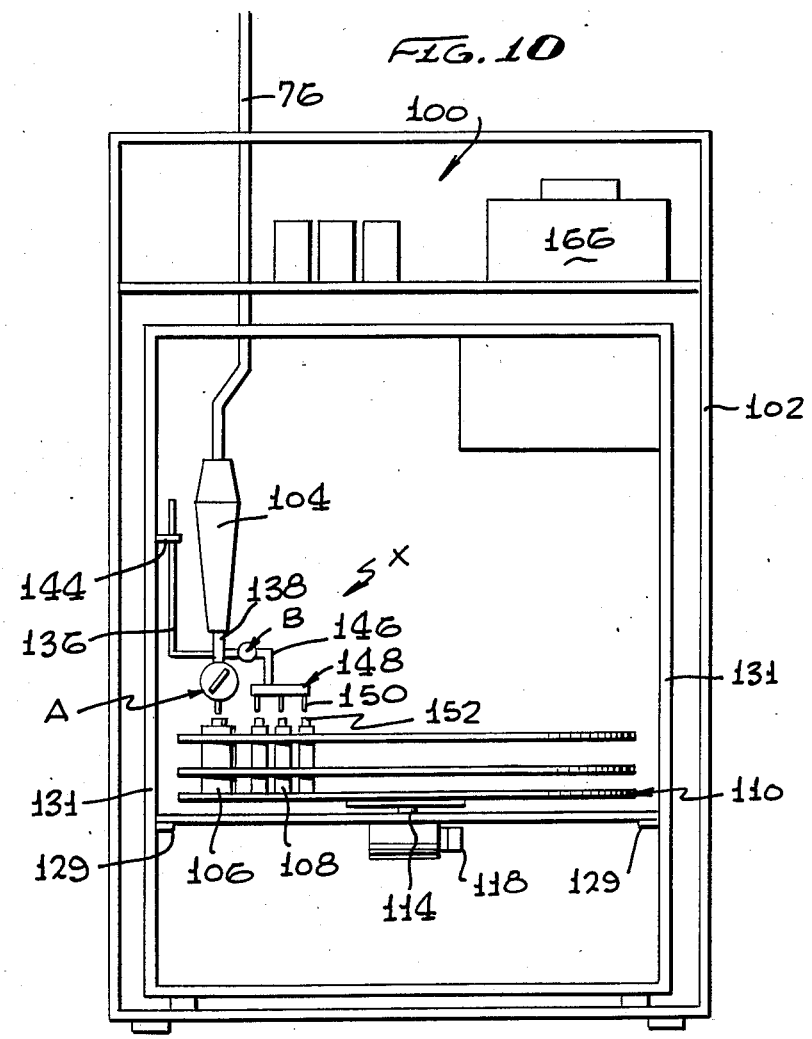

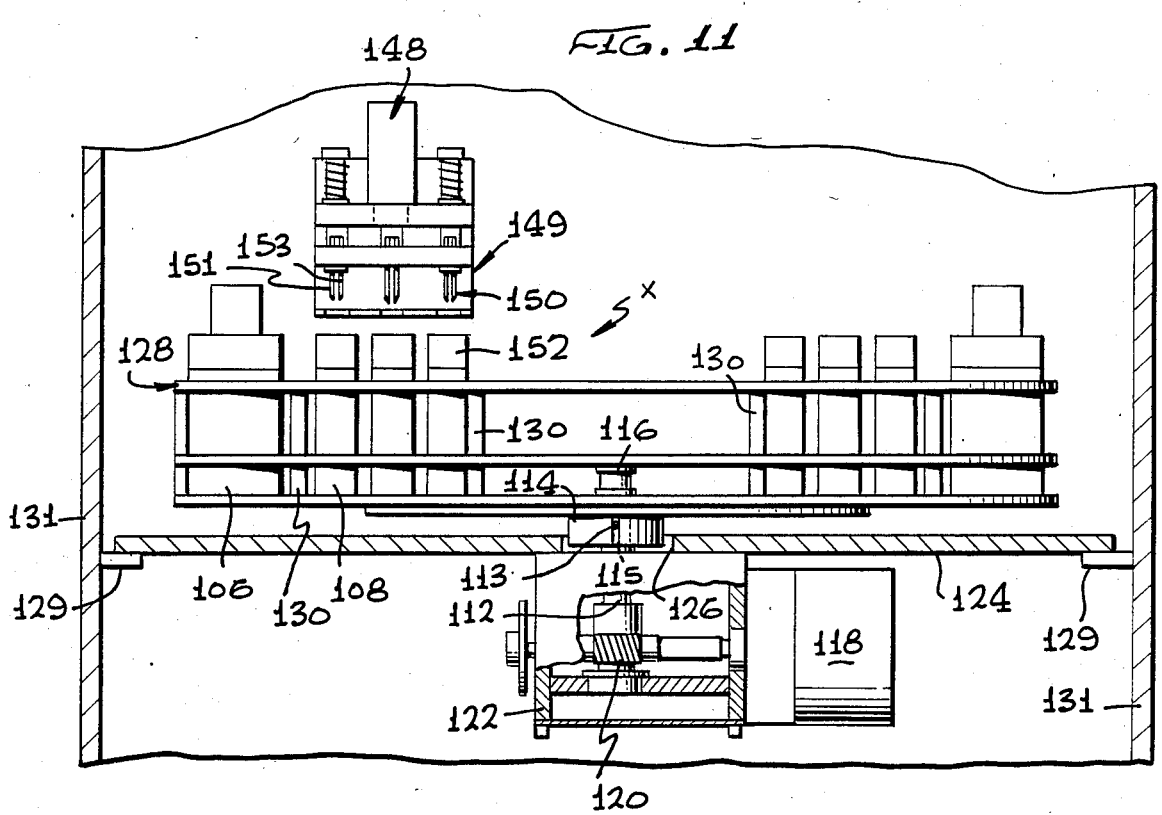
FIG. 11
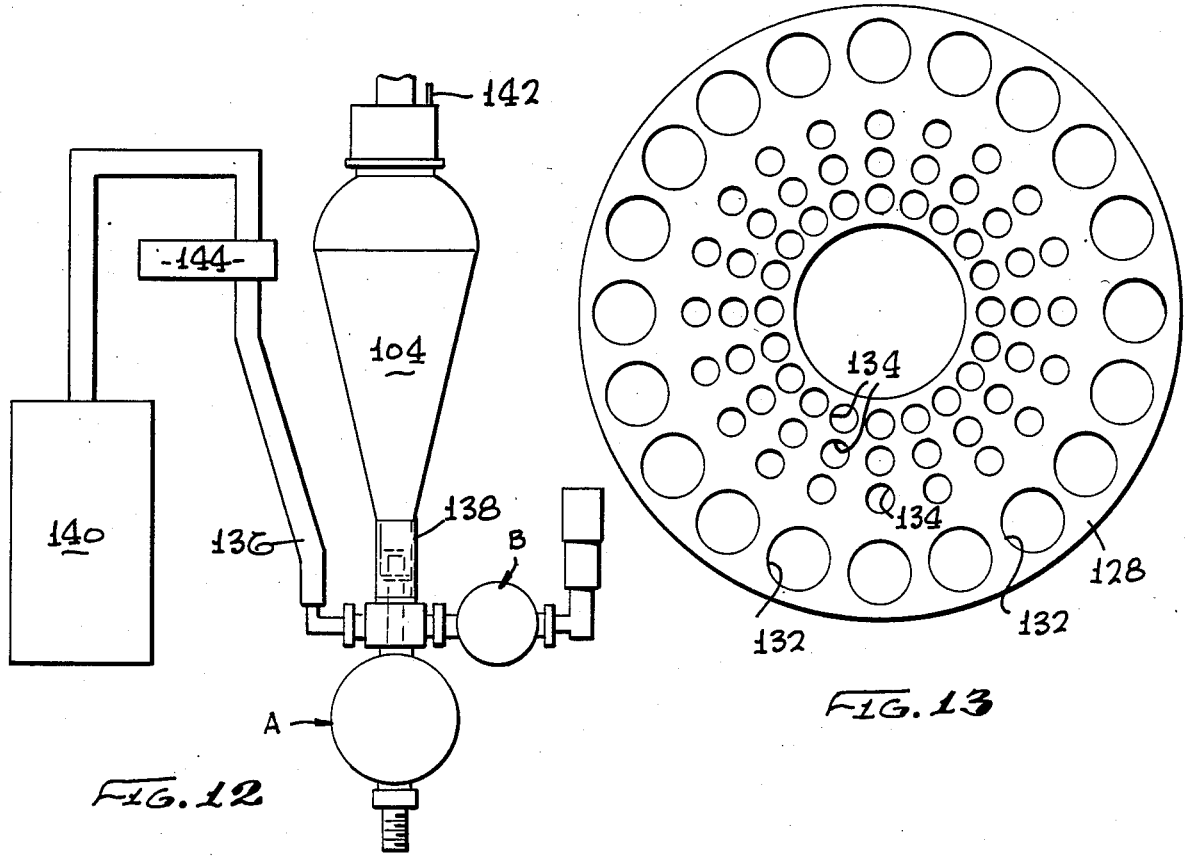
FIG. 12
FIG. 13

ACTIVE CLOUDWATER COLLECTOR

BACKGROUND OF THE INVENTION

This invention relates to the collection of fog water or cloud water and, more particularly, to the collection of cloud water by a device wherein cloud droplets impact upon Teflon strands and are funneled into a sample bottle.

Under supersaturated conditions in the atmosphere, fog droplets form by activation of condensation nuclei and rapidly grow to diameters of 1 to about 100 microns. Recent reports of extremely high acidities in fogs, and clouds intercepting mountain slopes, have raised concern regarding related environmental consequences. Air quality control agencies in areas exposed to acidic fog have expressed the need to establish networks of sites monitoring the chemical composition of fog on a routine basis.

Various types of fog water collectors have been designed, including use of a filter medium to capture the water on impaction and dripping from large obstacles, such as sails.

U.S. Pat. No. 3,889,532 discloses apparatus for collecting fog water consisting of a slotted rotatable tube. The tube is rotated, and fog droplets are collected by impaction on the tube. Centrifugal force causes the water to flow outward toward the ends of the tube where it is collected in small vials. However, the device of this patent presents safety problems and is not suitable for automation.

SUMMARY OF THE INVENTION

It is an object of the present invention to provide an improved cloud water collector which efficiently collects fog droplets in the 1 to 100 micron diameter range.

Another object of the invention is the provision of a cloud water collector of the above type capable of preserving the size and chemical composition of fog droplets through all stages of collection.

A still further object is to provide a cloud water collector which rapidly collects relatively large amounts of liquid cloud water for wet chemical analysis.

Yet, another object is to provide a cloud water collector which is inexpensive to construct, is reliable and requires minimal maintenance.

Another object is the provision of an efficient cloud water collector which can be automated and including means for automating such collector.

A still further object is to provide an automated sampler, which is particularly useful in combination with the above-noted cloud water collector, or which can be used for collection of rain water samples.

According to the invention, there is provided a cloud water collector comprised of a sampler duct, e.g., in the form of a square box, open at both ends, and having a fan at the back of the duct. The fan draws the cloud through the sampler from the front of the duct, and the droplets in the cloud are impacted on Teflon (polytetrafluoroethylene or a copolymer of tetrafluoroethylene and hexafluoropropylene) strands or filaments which are strung in the form of a screen on a frame. The screen formed of the Teflon strands is inclined at an acute angle, preferably about 35° from vertical, facing the front of the duct.

The droplets in the cloud impacting upon the Teflon strands of the screen are drawn down by both the air drag and by gravity to the bottom of the screen where the water droplets accumulate and are diverted to a sample bottle, and the collected bottle of water is then analyzed chemically.

In preferred practice, the Teflon strand diameter, the spacing of the strands forming the screen, and the angle of the screen have values which provide efficient and rapid collection of fog droplets in the 1 to 100 micron size range while avoiding collection of the sub-micron aerosol particles. Also, in preferred practice, a honeycomb element is provided between the fan and the screen of Teflon strands, to straighten the flow of the sample cloud throuoh the duct and provide uniform flow of the cloud sample across the duct and through the Teflon screen, to improve the performance of the collector.

The cloud water collector of the invention is easily constructed, inexpensive, and operates in a reliable manner.

The cloud water collector of the invention can be modified for automating the device so as to automatically collect successive cloud water samples. The automating means comprises a motor-driven turntable which holds a plurality of sample bottles. The cloud water sample provided by the cloud water collector is discharged into a reservoir having a liquid level sensor. When the reservoir is filled to the predetermined level, the sensor actuates a valve to open same and discharge the sample from the reservoir into one of the bottles on the turntable. The valve closes and the turntable then rotates to index the next bottle beneath the reservoir and the operation is repeated to fill the latter bottle with additional sample cloud water provided by the cloud water collector.

Alternatively, a timer can be employed instead of a liquid level sensor, which actuates a valve to discharge the cloud water sample from the reservoir into the bottle below the reservoir, when a pre-set time interval has elapsed. If desired, a combination of liquid level sensing and timer means can be employed, as described in greater detail below.

The automation device, per se, can also be employed for automatically collecting rain water samples instead of cloud water samples. When so employed, rain water is collected in a funnel and then directed to the reservoir from which it is automatically discharged into the sample bottles in the manner noted above.

BRIEF DESCRIPTION OF THE DRAWINGS

The invention will be more clearly understood by reference to the preferred embodiments set forth hereinafter, taken in conjunction with the accompanying drawings, wherein:

FIG. 1 is a side elevational view of a preferred cloud water collector according to the invention;

FIG. 1a is an enlarged elevational view of the front portion of the device of FIG. 1, showing the inclined screens formed of Teflon strands for collecting cloud water droplets;

FIG. 2 is a front view of the device of FIG. 1, taken on line 2—2 of FIG. 1, with the Teflon screens removed;

FIG. 3 is a rear view of the device of FIG. 1, taken on line 3—3 of FIG. 1, with the fan removed;

FIG. 4 is an elevational view of one of the screens of Teflon strands shown in FIG. 1a;

FIG. 4a is a side view of the Teflon screen of FIG. 4;

FIG. 5 is a plan view taken on line 5—5 of FIG. 1, showing the trough for cloud water sample collections;

FIG. 6 is a section taken on line 6—6 of FIG. 5;

FIG. 7 is a detail illustrating the means connected to the trough of FIG. 6 for discharging cloud water collected in the trough of FIG. 6, into a sample bottle;

FIG. 8 is an adapter inlet which can be connected to the front of the cloud water collector of FIG. 1, which prevents the larger rain droplets from entering the device;

FIG. 9 is a top view of the adapter inlet of FIG. 8;

FIG. 10 is a front elevation of the automated sampler employed in conjunction with the cloud water collector of FIGS. 1-9;

FIG. 11 is a detailed front elevational view of the carousel assembly for supporting the sample bottles, of FIG. 10;

FIG. 12 is another detail of the sampler device of FIG. 1, showing the collector reservoir and overflow device employed in conjunction therewith;

FIG. 13 is a plan view of the carousel or turntable of FIG. 11;

DESCRIPTION OF THE PREFERRED EMBODIMENTS

Figures 14, 15:
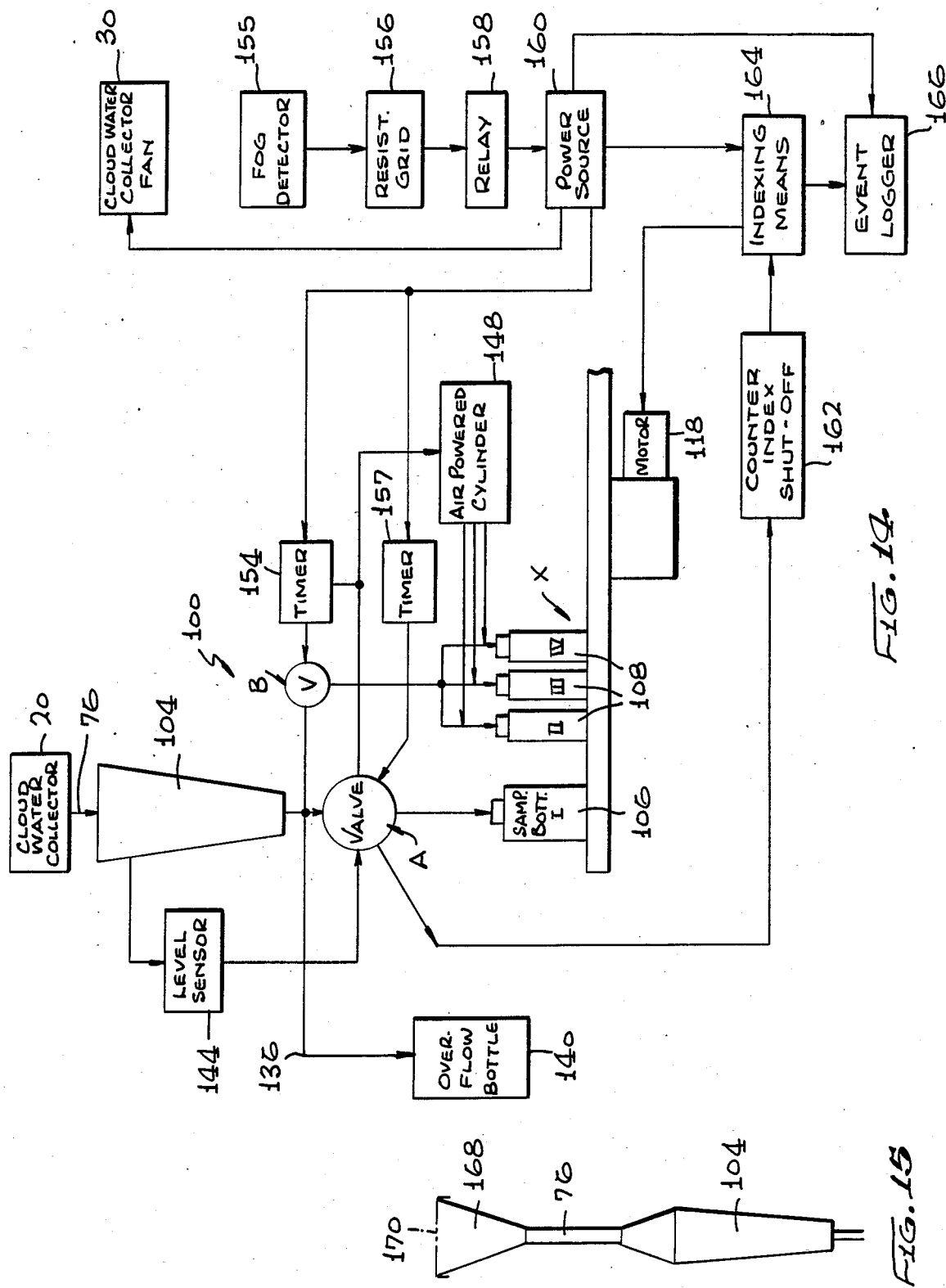
FIG. 14 is a block diagram of the associated elements for operating the automated sampler of FIG. 10.
FIG. 15 illustrates use of the automated sampler of FIG. 10 for collecting rain water samples.

Referring to FIGS. 1, 2 and 3 of the drawings, numeral 20 indicates a cloud water collector according to the invention, comprising an outer housing 21 having a front section 22 and a rear section 24, the front being open at 26 and the back of the collector being open at 28. The housing of collector 20 is in the form of a box having an essentially square cross-section, the rear section 24 of the collector being flared outwardly as indicated at 29 to accommodate a fan or blower 30 in a rear portion 32. The front and rear sections are provided with flanges 25 which are connected by bolts 27.

The outer housing 21 of the cloud water collector is preferably comprised of a clear poly (methyl methacrylate) resin (Plexiglas). Other clear inert plastics can be employed, such as polypropylene or polyethylene. However, the latter two materials tend to degrade in sunlight over a period of time.

Viewing also FIG. 1a, a series of three screens 34, each formed of two parallel rows of Teflon strands or filaments, and described in greater detail below, are mounted and inclined at an acute angle in the front section 22 of the collector, adjacent the open front end 26 thereof. A honeycomb element 36 is mounted across substantially the central portion of the collector between the front and rear sections 22 and 24 thereof.

The fan 30 is mounted on a bracket 38 which is suitably bolted at 40 to a support member 42 mounted on the back 28 of the collector.

Now referring to FIGS. 1a, 4 and 4a, the screens 34 are each formed of a rectangular frame 43 comprised of two stainless steel upper and lower rods 44, preferably Teflon coated, suitably fastened at their ends to opposite side bars 46. Stiffener webs 45 are positioned across frame 43 adjacent the rods 44 at the top and bottom of the frame and are suitably welded at 49 to the opposite side bars 46. The rods 44 are threaded at 47 to received a Teflon strand 48 which is wound around the rods 44 in a vertical direction along the entire width of the screen extending from one side bar 46 to the opposite side bar. It has been found that in order to obtain efficient collection of fog droplets of a size ranging from 1 to 100 microns in diameter, and particularly of droplets in the range of about 5 to about 30 microns, the main portion of fog droplets which impact and collect on the Teflon strands, a preferred diameter of the Teflon strands ranges from about 0.015" to about 0.025", an optimum strand diameter being 0.020".

The spacing between adjacent strands of the filament 48, and hence the spacing between the threads 47 receiving the strands, is preferably between 0.06" and 0.08", optimally about 0.070".

It is preferred to minimize the size or diameter of the Teflon filament while still maintaining it sufficiently large so that it is strong and durable and does not break over a long period of use. The space between adjacent strands mounted on the rods 44 of the frame 43 should be sufficiently large to permit free flow of the cloud water sample through the screen while permitting efficient impaction of fog droplets from the flow of the cloud sample, on the Teflon filaments. Referring to FIG. 1a, it will be noted that each of the screens 34 is comprised of two parallel rows 50 of the Teflon strands 48 mounted on the opposite rods 44.

Referring now to FIGS. 1 and 1a, the Teflon screens 34 are mounted at an acute angle, most particularly at an angle of 35° to the direction of the incoming flow of the cloud sample introduced through inlet 26. For this purpose, grooves 52 are provided in the opposite side walls 54 of the front section 22 of the collector, such grooves being inclined at a 35° angle to accommodate the side bars 46 of each of the Teflon screens 34 mounted in parallel inclined relation at such angle in the front section of the collector. It will be seen that in the present embodiment, three collector screens 34 are employed, mounted parallel to each other, and in closely spaced relation within the front section of the collector. The frames 43 of the screens are suitably fastened at 56 and 58 in brackets 60 and 62 mounted respectively in the top 64 and bottom 66 of the front section of the collector.

In the embodiment illustrated in FIGS. 1 and 1a employing three Teflon screens 34, since there are two rows of Teflon strands 50 for each screen, there is a total of six rows of Teflon strands in the three screen arrangements shown. In such an arrangement, with Teflon strands of the optimum diameter of 0.020" and a spacing of 0.070", the first row of strands on the first screen 34 facing the inlet 26 samples about 28% of the incoming cloud sample flow, and when all six rows of strands formed by the three screens are included, such six rows sample about 86% of the total air. While it is preferred not to employ more than three Teflon screens 34, only one or two of such screens can be employed if it is desired to slow the collection rate down.

Although the optimum angle of inclination of the screens is 35°, as noted above, the angle of the Teflon screens can range from about 30° to about 40°. Inclining the screens at such angles, particularly the optimum angle of 35°, prevents resuspension into the air flow of fog droplets impacted onto the Teflon filaments. Further, once the droplets are collected on the strands, it is desirable that they be removed from the environment of the sample flow as quickly as possible to prevent evaporation. The above-noted angle of inclination aids in obtaining rapid flow of the droplets down the filaments for collection as quickly as possible. A baffle 67 is provided and suitably connected to the top of the housing 21 and formed of a front downwardly sloping portion 69 which directs the incoming cloud sample downwardly away from the upper structure of the frames 43 including the upper rods 44, and a rear upwardly sloping portion 71, which deflects the air stream passing through screens 34 upwardly across the conduit formed by housing 21.

Referring to FIGS. 5, 6 and 7, a trough 68 is provided across the bottom 66 of the front section 22 of the collector, such trough being inclined downwardly from the opposite side walls 54 of the front portion 22, to the center thereof, as indicated at 70, and terminating in a central discharge outlet 72. A funnel 74 is positioned in the discharge outlet, to which is connected one end of a tube 76, the opposite end of the tube being connected to a sample bottle 78.

It will accordingly be seen that water droplets flowing down the Teflon filaments 48 of the six rows 50 of such strands provided by the three screens 34, will collect in the trough 68 and pass via the funnel 74 and tube 76 into the collection bottle 78.

In operation, the fan 30, which can conveniently operate on 12-14 volt D.C. current, draws a sample cloud through the open front end 26 of the collector and into contact with the Teflon filaments 48 of the screens, causing fog droplets to impact on and flow down the Teflon strands 48 of the screens 34. The velocity of flow can be of the order of about 9 meters per second. Droplets below a certain size pass between the Teflon filaments and are not collected thereon, while larger droplets above a certain size collect on the strands. Droplets in the range of 1 to 100 microns diameter are efficiently collected and, particularly, droplets in the size window of 5 to 30 microns in diameter. While droplets of a size of about 3.8 microns can be collected at 50% efficiency, droplets of the order of 10 microns size and above can be collected at practically 100% efficiency.

The honeycomb element 36 in FIGS. 1 and 3 functions as a flow straightener, that is, it produces uniform flow of the cloud sample across the collector and removes swirl and reduces turbulence created by the fan. Although the honeycomb element can be omitted, the presence of the honeycomb element positioned between the Teflon screens 34 and the fan 30 substantially improves the performance of the device. This arrangement also aids in reducing contamination of the cloud sample and facilitates introduction of a clean, non-contaminated cloud sample into the collector for impingement on the Teflon strands 48.

When the cloud water collector described above is to be employed for sampling during rain, a rain adapter shown in FIGS. 8 and 9 is attached to the front open end 26 of the collector.

The rain adapter indicated at 80 is in the form of a clear plastic member, such as poly (methyl methacrylate) (Lucite), having a downwardly sloping, closed top 82 connected to opposite sides 84 of triangular shape, the lower edges of which terminate in a horizontally positioned, open bottom 86. The inner end of the rain adapter 80 terminates in a square conduit 88 having a flange 90 mounted around its inner end.

The rain adapter 80 can be mounted on the front 26 of the cloud water collector by attaching the flange 90 of the adapter to the flange 92 on the front of the cloud water collector, by suitable fasteners, such as bolts. During the rain, while the air flow sample is drawn in through the open lower end 86 of the adapter, as indicated by the arrow 94, and into the front section of the cloud water collector for impingement on the Teflon screens 34, in the normal manner of operation as noted above, the larger rain droplets impinge on the top 82 of the rain adapter and flow down the top, but such droplets have too much inertia and are unable to be drawn upwardly through the open bottom 86 and into the adapter and the collector, with the air or cloud sample to be collected.

Typical operating parameters for the cloud water collector of the invention described above and shown in the drawings are set forth in the following table:

TABLE

| CLOUD WATER COLLECTOR OPERATING PARAMETERS | |
| --- | --- |
| Strand dia., $\mu$m (in.) | 510 (0.020) |
| Strand length, m (ft.) | 190 (620.0) |
| Sampling flow, m3/min. (cfm) | 24.5 (870) |
| # of rows of strand | 6 |
| Strand spacing, mm (in.) | 1.8 (0.071) |
| % of air sampled, 1st row | 27.9 |
| % of air sampled, total | 86.0 |
| Total sampled flow, m3/min | 21.1 |
| 50% size cut (theor.), $\mu$m | 3.8 |
| Stokes number (10 $\mu$m droplet) | 8.4 |
| Inlet velocity, m/s | 7.0 |
| Velocity @ strands, m/s (MPH) | 8.45 (18.9) |
| Coll. rate in 0.5 g/m3 fog, 10 $\mu$m droplets, ml/min. | 9.95 |
| Operating voltage, v. | 14.0 |

The cloud water collector of the invention described above and illustrated in FIGS. 1 to 9 of the drawings can be operated manually so that when a sample bottle of cloud water liquid is filled, it is removed from the apparatus and another bottle is manually connected to the device for collecting another sample, and so on. However, it is often preferred to automate the device so that each sample bottle, when filled with cloud water liquid, is automatically removed from the device and a new bottle arranged in its place to collect the next sample. This permits the cloud water collector to be set up in the field and left to automatically collect the fog water samples, thus providing manpower savings.

Accordingly, there is described below and shown in FIGS. 10 to 14 of the drawings a preferred embodiment of a device which can be employed in conjunction with the cloud water collector described above for automating the collector and obtaining multiple samples of cloud water for chemical analysis.

Referring to FIGS. 10-13 of the drawings, numeral 100 is an automated sampler device, according to the invention, which can be employed in conjunction with the cloud water collector 20 of FIG. 1 for obtaining samples of cloud water collected in collector 20. Preferably, the automated sampler 100 is incorporated in a refrigerator 102 which aids in maintaining the chemical composition of the cloud water samples without change, for example, as a result of evaporation. However, it will be understood that the use of a refrigerator for the automated sampler hereof is not necessary.

When employing the automated sampler 100, the sample collection tube 76 of the cloud water collector, as seen in FIG. 7, is connected directly to a reservoir 104, which is arranged to discharge a predetermined volume of collected cloud water via a valve A sequentially into a plurality of large sample bottles 106, and via a valve B sequentially into a plurality of small sample bottles 108 supported on a turntable or carousel 110, which is rotated by a shaft 112 connected to a central support block 114 attached to the center of the carousel by the fastener 116. The shaft 112 and central support block 114 are interconnected by a pair of oppositely disposed pins 113 on the shaft 112, which are received in oppositely disposed slots 115 in the lower portion of the support block 114. The shaft 112 and support block 114 are driven by a motor 118 through a worm gear 120 mounted in a centrally positioned frame 122. The shaft 112 and central support block 114 are received in a central aperture 126 of a support member 124 to maintain the carousel in a substantially central position during operation. The frame 122 is connected to the support member 124 by suitable fasteners (not shown), and hence, the support member supports the frame 122, motor 118 and carousel 110. The support member 124 is mounted at opposite ends on outer support blocks 129 attached to opposite side walls 131 of the refrigerator.

A series of large sample bottles 106 is mounted circumferentially adjacent the outer periphery of the carousel in a circular rack 128 supported on the carousel by support pins 130. The large bottles 106 are each positioned in circular holes 132 provided adjacent the outer periphery of the rack. In the embodiment shown, there are 20 such holes 132 for receiving 20 of the large bottles 106, e.g., of 60 mls capacity each.

There are also provided in the rack 128 three concentric circles of smaller holes 134 for receiving the small bottles 108, there being 20 of the small holes 134 in each of the three concentric circles of holes, for receiving 20 of the small bottles 108, e.g., having a capacity of 8 ml each in the present embodiment.

It will accordingly be seen that at the sample bottle-filling station X, as shown in FIGS. 10 and 11, there will be one large sample bottle 106 and three oppositely disposed small bottles 108.

Referring to FIG. 12, an overflow line 136 is connected to the discharge conduit 138 from the bottom of reservoir 104, such overflow conduit discharging into an overflow bottle 140. A vent 142 is provided at the top of the reservoir 104. A liquid level sensor 144, in the form of a photoelectric cell, is provided to monitor a predetermined volume of cloud water received in the reservoir 104.

Now referring to FIGS. 10 and 11, an auxiliary line 146 is connected to the discharge conduit 138, a valve B being disposed in the discharge line 146, for actuation to fill three of the small bottles 108, simultaneously with actuation of valve A for filling one of the large bottles 106 at the filling station X. An air cylinder powered device 148 is arranged to actuate a sliding assembly 149 carrying three hypodermic needles 150 communicating with line 146. Each of the needles 150 has a fluid inlet 151 communicating with the line 146 and a vent tube 153. Each of such needles pierces a septum 152 which tops each of the small bottles 108 when the support assembly 149 is urged downwardly. The air powered assembly is actuated by the opening of valve A, at which time valve B is also opened for filling the three small bottles 108 through the hypodermic needles.

Now referring also to FIG. 14, showing a block diagram of the automated sampler 100, it will be noted that a timer 154 is connected to valve B for introducing a predetermined amount of sample liquid from the reservoir 104 into each of the three small sample bottles 108, simultaneously during the filling of the large bottle 106 via valve A at the filling station X.

The automated sampler 100, when set up to collect cloud water samples in conjunction with the cloud water collector 20, operates as follows:

A fog detector indicated at 155, which is basically a miniature version of the cloud water collector 20, is actuated, and when fog is present, such fog detector collects a sample amount of the fog water and deposits it onto a resistance grid, indicated at 156. A circuit (not shown) senses the charge on the resistance grid 156, due to the presence of the fog water, and trips a relay 158 which supplies power from power source 160 to the various components in the device, as noted below, including fan 30 of the cloud water collector 20.

Fog water collected in the cloud water collector 20 is discharged via tube 76 into the reservoir 104. According to one mode of operation, when the liquid sample collected in the reservoir 104 reaches a predetermined volume, as indicated by the level sensor 144, the sensor actuates the valve A to open same to discharge the liquid sample into the bottle 106 at the fill station X. Simultaneously with the opening of valve A, a timer indicated at 154 opens valve B to discharge liquid from reservoir 104 via hypodermic needles 150 into each of the three small sample bottles 108 at station X. In one example of operation, valve B remains open for about 5 seconds to discharge a total of 15 ml of sample liquid (5 ml per bottle) in the three small 8 ml bottles 108. During this same period of time, sample liquid flows from reservoir 104 into the large 60 ml sample bottle 106. The timer 154 then closes valve B. However, valve A remains open to discharge the remainder of the liquid in reservoir into the large bottle 108. If the pre-set volume of liquid collected in reservoir 104 is 60 ml, then 45 ml of liquid is collected in a total period of 20 seconds in the large 60 ml sample bottle 106. When the reservoir 104 is emptied, valve A closes to permit the reservoir 104 to again fill with cloud water. When valve A closes, the air powered cylinder is actuated to withdraw the hypodermic needles 150 from the small bottles to the position shown in FIG. 11.

According to a second mode of operation, a timer 157 is employed in conjunction with valve A, instead of level sensor 144. In this mode of operation, the timer 157 times the interval for filling the reservoir 104, say, one hour. This is the "off" interval of the timer 157. At the end of such time, the timer actuates the valve A, while at the same time, the timer 154 actuates the valve B, to fill the large bottle 106 and the small bottles 108 simultaneously. During this filling operation of about 20 seconds, the timer 157 is in the "on" interval. The timer 157 then switches to the "off" interval again, closing valve A, while timer 154 closes valve B, to permit reservoir 104 to again be filled with sample liquid.

In a third mode of operation employing both the level sensor 144 and the timer 157, for actuating valve A, if either the time has elapsed as set by timer 157, for filling the reservoir 104 to a predetermined volume, or the collected volume of liquid as indicated by the level sensor 144 has been achieved, whichever occurs first, valve A will be opened by either the level sensor or the timer 157, to permit discharge of liquid into the large bottle 106, while at the same time simultaneously the timer 154 opens valve B to permit discharge of liquid sample into the small bottles 108, after which valves A and B are closed, as noted above, to permit repeated filling of the reservoir 104. This third mode of operation is preferred.

After the accumulated liquid has been discharged from the reservoir 104 into the sample bottles at filling station X, and valves A and B have been closed, a counter, indicated at 162, which is responsive to the closing of valve A, actuates an indexing mechanism 164, which in turn actuates the motor 118 and worm gear 120 to rotate the carousel a predetermined amount so as to move the filled bottles from the filling station X and to advance the next row comprised of one large bottle 106 and three small bottles 108 into position at the filling station X. The above-described operation for filling the large bottle 106 and the small bottles 108 at fill station X is repeated until all of the 20 large bottles and 60 small bottles on the carousel are filled. At the end of this time, the counter 162 shuts off power to the indexing mechanism 164 and causes diversion of liquid filling the reservoir 104, through the overflow tube 136 and into the overflow bottle 140.

An event logger (printer) 166 records the time when sampling begins and when the carousel indexes to a new position.

It will be understood that, if desired, the automated sampler can be used for filling only the large sample bottles 106 and omitting the small sample bottles 108. Under the circumstances, components for filling the small bottles, including valve B and its associated timer 154, the auxiliary discharge line 146, air cylinder 148, and the hypodermic needle devices 150 can be omitted.

Further, if desired, the above-described mechanism for actuating the automated sampler, including the small fog detector 155, and its associated resistance grid 156 and relay 158 can be omitted, and the power source at 160 can be turned on manually or by any other means at any desired time.

In addition, the automated sampler 100 can be employed separately, that is, without combining it with the cloud water collector 20, e.g., for collecting rain water. In the latter case, viewing FIG. 15, a rain water collecting funnel 168 can be connected to the tube 76 for discharge of a sample of rain water into the liquid reservoir 104. The automated sampler then functions in the manner described above for collecting multiple samples of the rain water so collected. When not in use for collecting rain water, a cover indicated by dotted lines 170 can be placed over the funnel.

From the foregoing, it is seen that the invention provides an improved device for collecting cloud water or fog water for chemical analysis which operates efficiently and rapidly to collect substantial amounts of liquid water for chemical analysis, and which is reliable, simple to construct and inexpensive. In addition, the cloud water collector can be automated by use in combination with an automated sampler device to collect multiple samples of fog water in the field, with a minimum of attention and labor expense. Further, the automation device can be employed separately for collecting rain water.

Since various additional changes and modifications of the invention will occur to and can be made readily by those skilled in the art without departing from the invention concept, the invention is not to be taken as limited except by the scope of the appended claims.

What is claimed is:

1. A cloudwater collector comprising
a conduit open at opposite ends, including an air inlet at a front end thereof to permit entry of a cloudwater containing air sample into said conduit, and an air outlet at the opposite back end thereof,
a plurality of spaced Teflon strands in said conduit adjacent the front end thereof, said strands being mounted across said conduit at an acute angle facing said inlet,
the diameter of said strands being such that water droplets from a cloudwater sample, of a size range of 1–100 microns are collected on the strands upon impact therewith, said acute angle being such that the impacted droplets flow down said strands and drain into the bottom of said conduit,
a fan at the back end of said conduit adjacent said air outlet for drawing a sample of air containing cloudwater through said inlet into said conduit,
means for reducing turbulence and producing essentially uniform flow of said air sample across said conduit, and
means for collecting a sample of the water droplets from the bottom of said conduit.

2. The cloudwater collector of claim 1, said Teflon strands being wound in vertical spaced relation on a frame and forming a screen containing two parallel rows of said strands on said frame.

3. The cloudwater collector of claim 2 including a plurality of said screens mounted in spaced parallel relation at said acute angle across said conduit.

4. The cloudwater collector of claim 2, said Teflon strands and said screen being mounted at an angle of 30°–40° across said conduit facing said inlet.

5. The cloudwater collector of claim 2, said Teflon strands having a diameter such that water droplets from a cloudwater sample, of a size ranging from 5–30 microns, are efficiently collected on the Teflon strands.

6. The cloudwater collector of claim 2, said Teflon strands having a diameter ranging from 0.015″ to 0.025″.

7. The cloudwater collector of claim 1, said means for reducing turbulence and producing essentially uniform flow of said air sample across said conduit comprising a honeycomb element mounted across said conduit between said Teflon strands and said fan.

8. The cloudwater collector of claim 1, said means for collecting said water droplet sample comprising a drain in the bottom of said conduit, a funnel connected to said drain, a sample bottle, and tube means communicating said funnel with said sample bottle.

9. The cloudwater collector of claim 1 including a frame for said Teflon strands, said frame having upper and lower threaded rods, said Teflon strands wound on said threaded rods in vertical spaced relation, and forming a screen containing two parallel rows of said strands on said frame, and including a plurality of said screens mounted in spaced parallel relation, said Teflon strands and said screens being mounted at an angle of 35° across said conduit facing said inlet.

10. The cloudwater collector of claim 9, said Teflon strands having a diameter of about 0.020″ and a spacing between strands of about 0.070″.

11. The cloudwater collector of claim 10, said means for reducing turbulence comprising a honeycomb element mounted across said conduit between said Teflon strands and said fan, and said means for collecting said water droplet sample comprising a drain in the bottom of the said conduit, a funnel connected to said drain, a sample bottle, and a tube communicating said funnel with said sample bottle.

12. The cloudwater collector of claim 1 including means for automating the collection of successive cloud water samples, said automating means comprising a reservoir in fluid communication with said sample collecting means, turntable means adapted to support a plurality of containers thereon, means associated with said reservoir for automatically discharging a predetermined volume of cloudwater from said reservoir into a preselected container on said turntable means, and means to actuate said turntable means to index a successive container to be filled into operative relation with said reservoir when said preselected container has received said predetermined volume of cloudwater.

13. The cloudwater collector of claim 12, said automatic discharge means comprising valve means operable to open when said predetermined volume of cloudwater has been collected to discharge same into said container, said turntable indexing means being actuated when said valve means is closed.

14. The cloudwater collector of claim 12, said automatic discharge means comprising a liquid level sensor for said reservoir and valve means associated with said liquid level sensor, said liquid level sensor actuating said valve means when said reservoir is filled with cloudwater to a predetermined level to discharge the cloudwater from said reservoir into said preselected container.

15. The cloudwater collector of claim 12, said automatic discharge means comprising timer means for timing the flow of cloudwater into said reservoir over a preselected time interval and valve means associated with said timer means, said timer means actuating said valve means after said preselected time interval, to discharge the cloudwater from said reservoir into said preselected container.

16. The cloudwater collector of claim 12, said automatic discharge means comprising a liquid level sensor for said reservoir and valve means associated with said liquid level sensor, said liquid level sensor actuating said valve means when said reservoir is filled with cloudwater to a predetermined level to discharge the cloudwater from said reservoir into said preselected container, and also including timer means for timing the flow of cloudwater into said reservoir over a preselected time interval and valve means associated with said timer means, said timer means actuating said valve means after said preselected time interval, to discharge the cloudwater from said reservoir into said preselected container, said liquid level sensor or said timer means actuating its associated valve means to discharge the cloudwater from said reservoir after said predetermined volume is achieved or said preselected time interval has elapsed, whichever occurs first.

17. The cloudwater collector of claim 12 including means for deactivating said turntable indexing means when all of the containers on said turntable have been filled, and means for thereafter diverting incoming cloudwater from said reservoir to an overflow container.

18. The cloudwater collector of claim 12 including means for actuating said automating means when cloudwater is present, for discharge of sample liquid from the sample collecting means of said cloudwater collector, to said reservoir.

19. The cloudwater collector of claim 12, said means for automatically discharging a predetermined volume of cloudwater from said reservoir including, a first valve means, a second valve means, means for actuating said first valve means when said predetermined volume of cloudwater has been collected in said reservoir to open and fill a first container at a fill station on said turntable, timer means for actuating said second valve means when said first valve means has been actuated, to open and fill a second smaller container at said fill station on said turntable, said timer means closing said second valve means after a pre-set time interval, and said means for actuating said first valve means closing same after a longer pre-set time interval, and means for sensing the closing of said first valve means, to actuate said indexing means to index successive first and second containers for advancement to said fill station.

20. The cloudwater collector of claim 19, said means to actuate said first valve means including a liquid level sensor means to monitor collection of said predetermined volume of cloudwater in said reservoir, and means associated with said liquid level sensor means to actuate said first valve means.

21. The cloudwater collector of claim 19 including a timer means to monitor collection of said predetermined volume of cloudwater in said reservoir, and means associated with said last-mentioned timer means to actuate said first valve means.

22. The cloudwater collector of claim 19 including a rack on said turntable adapted to support a plurality of said first containers in a circle adjacent the outer periphery of said turntable and a plurality of said second smaller containers in a concentric circle adjacent said first containers.

23. The cloudwater collector of claim 1, including means for automating the collection of successive cloudwater samples, said automating means comprising a reservoir in fluid communication with said sample collecting means, a carousel, means supporting said carousel for limited rotation, a rack on said carousel adapted to support a plurality of first sample bottles in a circle adjacent the outer periphery of said carousel and a plurality of second smaller sample bottles in concentric circles adjacent said circle of first containers, a fill station on said carousel wherein one of said first bottles and a plurality of said second bottles in said concentric circles are in a row, a discharge line from said reservoir, a first valve in said discharge line adapted to discharge liquid from said reservoir into one of said first bottles at said fill station, a second valve in said discharge line adapted to discharge liquid from said reservoir into the second bottles in said row at said fill station, a liquid level sensor to monitor collection of a predetermined volume of cloudwater in said reservoir, means associated with said liquid level sensor to actuate said first valve means when said predetermined volume of cloudwater has been collected in said reservoir to open and fill a first bottle at said fill station, timer means for actuating said second valve when said first valve has been actuated, to open and fill the second bottles in said row at said fill station, said timer means closing said second valve after a pre-set time interval, and said means for actuating said first valve closing same after a longer pre-set time interval, driving means to actuate the carousel to index a successive row of a first bottle and a plurality of second bottles at said fill station, means for sensing the closing of said first valve to actuate said driving means to index a successive row of bottles at said fill station, said last-mentioned means including a counter for deactivating said driving and indexing means when all of the bottles on said carousel have been filled at said fill station, an overflow tubing connected to the discharge line from said reservoir, and an overflow bottle connected to said overflow tube, for receiving liquid from said reservoir after deactivation of said driving and indexing means by said counter.

24. The cloudwater collector of claim 23, and also including timer means for timing the flow of cloudwater into said reservoir over a preselected time interval to actuate said first valve after said pre-set time interval, to discharge cloudwater from said reservoir into said first bottle at said fill station, said liquid level sensor or said last-mentioned timer means actuating said first valve to discharge the cloudwater from said reservoir after said predetermined volume is achieved or said preselected time interval has elapsed, whichever occurs first.

25. The cloudwater collector of claim 23, said second smaller bottles having a septum cover thereon, and means for piercing said septum bottles at the fill station for introduction of sample liquid to said bottles when said second valve has been opened.

* * * * *